US00PP36672P2

(12) United States Plant Patent
Chaussard

(10) Patent No.: US PP36,672 P2
(45) Date of Patent: May 13, 2025

(54) ***HIBISCUS* PLANT NAMED 'Minsygdrou02'**

(50) Latin Name: *Hibiscus syriacus*
Varietal Denomination: Minsygdrou02

(71) Applicant: Pierre Chaussard, Saint Mathurin sur Loire (FR)

(72) Inventor: Pierre Chaussard, Saint Mathurin sur Loire (FR)

(73) Assignee: HORTIVAL DIFFUSION, Beaufort en Anjou (FR)

( * ) Notice: Subject to any disclaimer, the term of this patent is extended or adjusted under 35 U.S.C. 154(b) by 0 days.

(21) Appl. No.: 18/913,560

(22) Filed: Oct. 11, 2024

(30) Foreign Application Priority Data

Jul. 8, 2024 (QZ) ..... PBR 20241609

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — Penny J. Aguirre

(57) ABSTRACT

A new cultivar of *Hibiscus* named 'Minsygdrou02' that is characterized by its large sized semi-double flowers that are deep pink-red in color, its flowers with small sized petaloids, its upright plant habit and its vigorous growth habit.

2 Drawing Sheets

Botanical classification: Hibiscus syriacus.
Cultivar designation: 'Minsygdrou02'.

CROSS REFERENCE TO A RELATED APPLICATIONS

This application is related to a European plant breeders' rights application filed on Jul. 8, 2024, application No. 2024/1609. There have been no offers for sale anywhere in the world more than one year prior to the filing of this Application and no accessibility to one of ordinary skill in the art could have been derived from the printed plant breeder's rights documents. The information in the plant breeder's rights application was obtained directly from the Inventor.

BACKGROUND OF THE INVENTION

The present invention relates to a new and distinct cultivar of *Hibiscus* plant, botanically known as *Hibiscus syriacus* 'Minsygdrou02', and will be referred to hereafter by its cultivar name, 'Minsygdrou02'. 'Minsygdrou02' is a new cultivar of rose of Sharon, a deciduous shrub grown for use as a landscape plant.

The new cultivar of *Hibiscus* arose from a breeding program conducted by the Inventor in La Ménitré, France. The goal of the breeding program was to develop a new cultivar of *Hibiscus* with large flowers that are deep pink-red in color. 'Minsygdrou02' originated as a cross made in August of 2012 between an unpatented and unnamed *Hibiscus syriacus* plant from the Inventor's breeding program, reference no. 259148, as the female parent and *Hibiscus syriacus* 'Freedom' (not patented) as the male parent. 'Minsygdrou02' was selected as a single unique plant in October 2014 from the resulting seedlings from the above cross.

Asexual propagation of the new cultivar was first accomplished by grafting in La Ménitré, France in February of 2015 by the Inventor. Asexual propagation by grafting and stem cuttings has determined that the characteristics of the new cultivar are stable and are reproduced true to type in successive generations.

SUMMARY OF THE INVENTION

The following traits have been repeatedly observed and represent the characteristics 'Minsygdrou02'. These attributes in combination distinguish 'Minsygdrou02' as a new and distinct cultivar of *Hibiscus*.

1. 'Minsygdrou02' exhibits large sized semi-double flowers that are deep pink-red in color.
2. 'Minsygdrou02' exhibits flowers with small sized petaloids.
3. 'Minsygdrou02' exhibits an upright plant habit.
4. 'Minsygdrou02' exhibits a vigorous growth habit.

The female parent plant of 'Minsygdrou02' differs from 'Minsygdrou02' in having flowers that are more pink in color and a less vigorous growth habit. The male parent of 'Minsygdrou02' differs from 'Minsygdrou02' in having flowers that are smaller in size with more numerous petaloids and a less vigorous growth habit. 'Minsygdrou02' can be most closely compared to *Hibiscus syriacus* cultivars 'Rwoods5' (U.S. Pat. No. 29,683) and 'Minsyrou17' (U.S. Pat. No. 33,258). Both are similar to 'Minsygdrou02' in having flowers that are similar in color. 'Rwoods5' differs from 'Minsygdrou02' in having a less vigorous growth habit, flowers that are smaller in size with more petaloids, and a semi-upright growth habit. 'Minsyrou17' differs from 'Minsygdrou02' in having smaller flowers that are single with no petaloids and a less vigorous growth habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Pepinieres Minier and Le Rose di Firenze.

BRIEF DESCRIPTION OF THE DRAWINGS

The accompanying colored photographs illustrates the overall appearance and distinct characteristics of the new *Hibiscus*. The photographs were taken of plants 8 years in age as grown outdoors in a trial garden in La Ménitré, France.

The photograph in FIG. 1 provides a side view of 'Minsygdrou02' in bloom.

Figure 1:
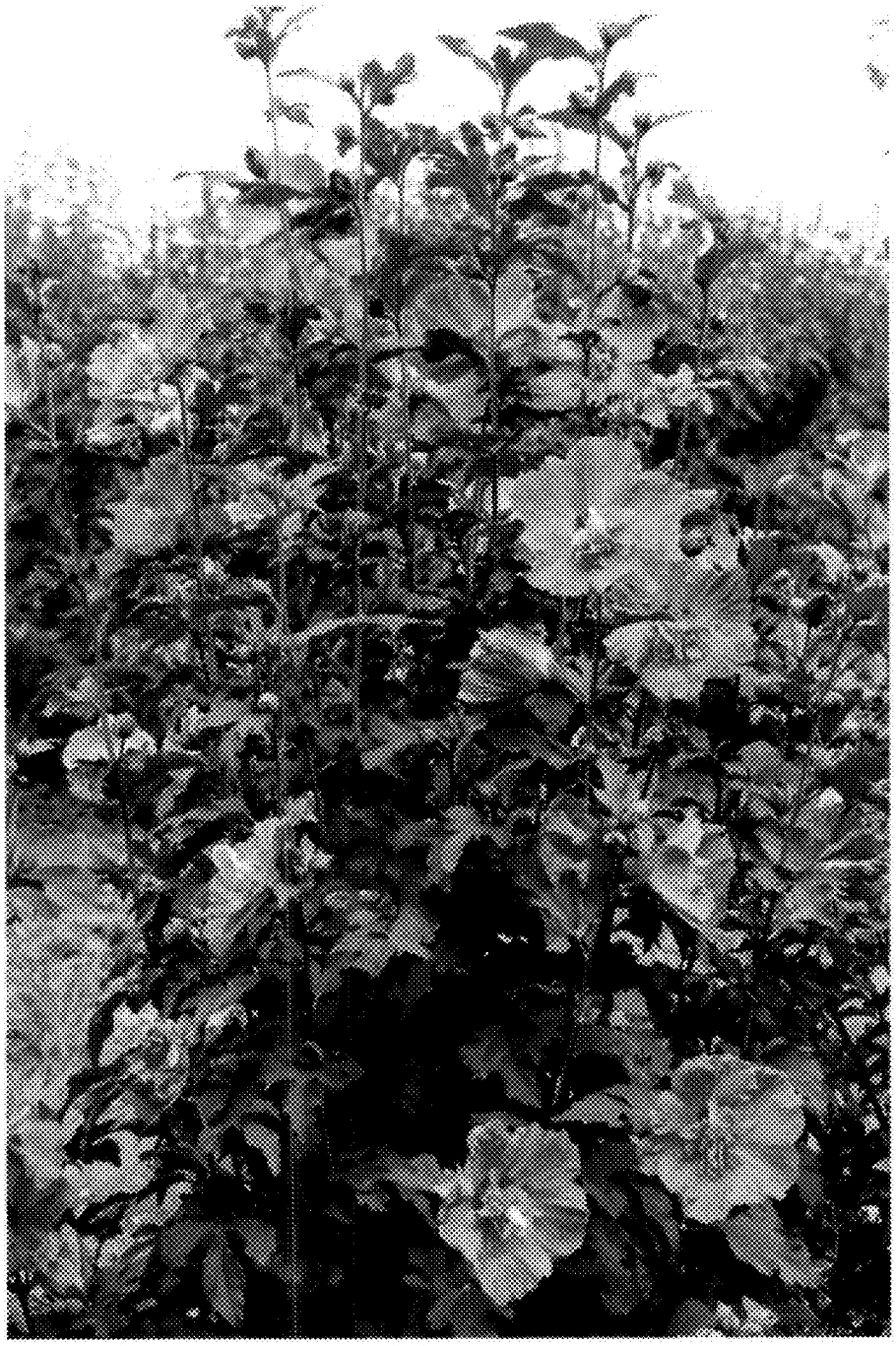
Figure 2:
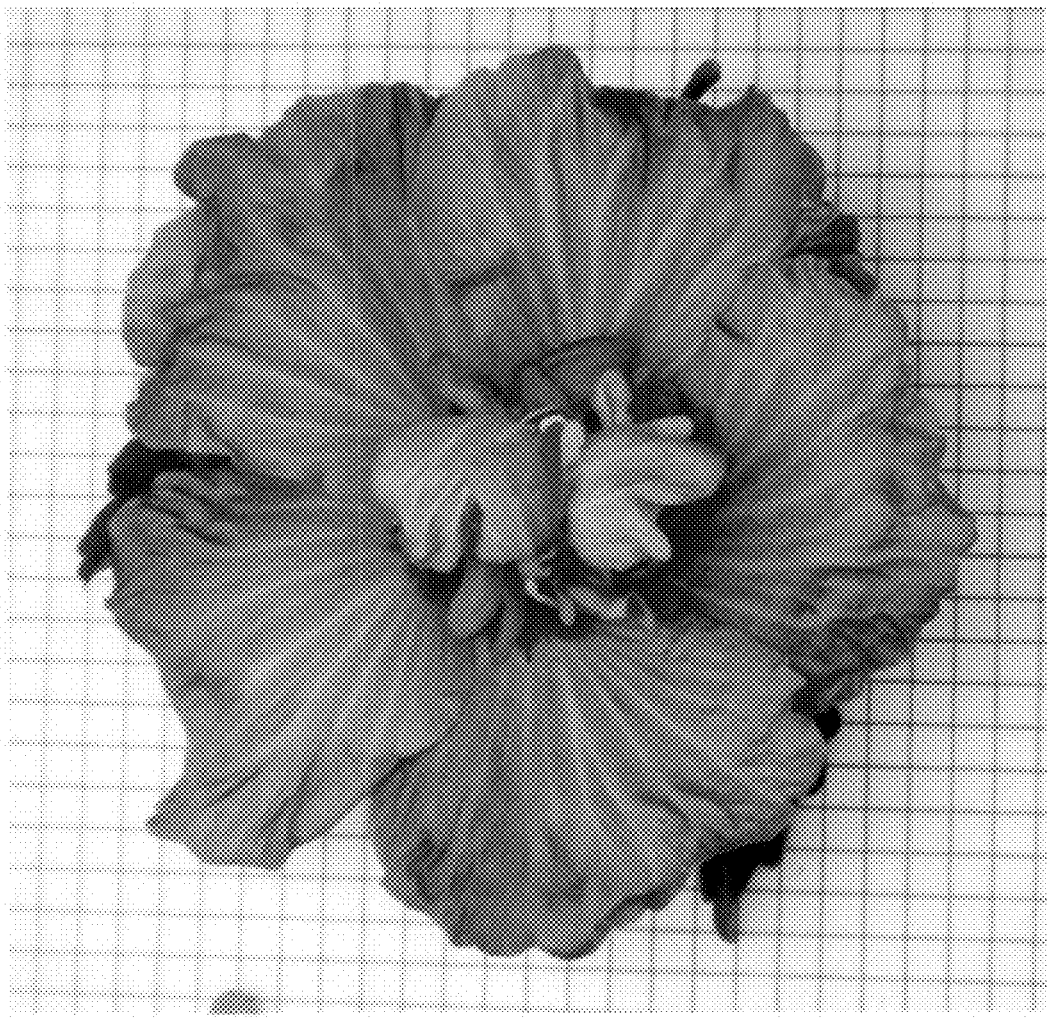

The photograph in FIG. 2 provides a close-up view of a flower of 'Minsygdrou02'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 4 year-old plants of the new cultivar as grown in three-gallon containers in a greenhouse and outdoors in Cottage Grove, Minnesota. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period.*—From the end of July to the end of October in La Ménitré, France.

*Plant type.*—Deciduous shrub.

*Plant habit.*—Upright.

*Height and spread.*—Reaches about 72 cm in length and 38 cm in width as a 4-year-old tree grown in a container, reaches 1.5 m in height and 80 cm in spread as a 4 mature plant in the landscape.

*Cold hardiness.*—At least to U.S.D.A. Zone 4.

*Diseases and pests.*—No susceptibility or resistance to diseases or pests has been observed.

*Root description.*—Fibrous roots 161B in color.

*Root development.*—About 33 days to produce a young rooted plant from a graft.

*Propagation.*—Grafting.

*Growth rate.*—Vigorous.

Stem description:

*Shape.*—Slightly oval.

*Stem color.*—New growth; 137B, lateral and secondary stems; a blend of 137B and 161B, mature wood; striations of 137B and 161B.

*Stem size.*—Main stem; an average of 12 cm in length and 1.3 cm in width (10 cm above the soil line), lateral stems; an average of 45 cm in length and 6 mm in diameter, secondary stems; an average of 33 cm in length and 4 mm in width.

*Stem surface.*—New growth; sparsely pubescent, maturing wood; smooth and puberulent, old wood (main stems); smooth with striations.

*Stem aspect.*—Lateral held upright with secondary stems held an average to 20° (vertical 0°).

*Stem strength.*—Very strong.

*Branching.*—An average of 1 main stems, 4 lateral stems per main branch, and 1 to 4 secondary stems per lateral branch.

*Internode.*—Average of 3.5 cm.

*Lenticels.*—Present on lower part of lateral stems and main stems, 161D in color, an average of 20 per stem section that is 3 cm in length and 5 mm in width, horizontal, oblong in shape, 0.7 mm in length.

Foliage description:

*Leaf shape.*—Broadly lanceolate overall.

*Leaf division.*—Simple.

*Leaf base.*—Cuneate.

*Leaf apex.*—Acute.

*Leaf venation.*—Palmate, color on mature leaves; 137B on upper surface and 138B on lower surface.

*Leaf margins.*—Tri-lobed, moderately deeply lobed, lobes serrate crenate.

*Leaf attachment.*—Petiolate.

*Leaf arrangement.*—Alternate and occasionally up to 5 leaves in a whorl at some nodes (typically lower nodes).

*Leaf orientation.*—Held horizontal to slightly downward from petiole.

*Leaf aspect.*—Slightly curled downward.

*Leaf surface.*—Upper surface glabrous and dull, lower surface glabrous with slight sheen.

*Leaf color.*—Young leaves; upper surface 137B, lower surface 138A, mature leaves; upper surface; NN137A, lower surface; 137B, variegation absent.

*Leaf size.*—Average of 6 cm in length and 4.4 cm in width.

*Leaf quantity.*—Average of 9 leaves per lateral branch 30 cm in length.

*Petioles.*—Average of 2.5 cm in length and 1.5 mm in diameter, 137B in color, pubescent surface.

*Stipule.*—None observed.

Flower description:

*Inflorescence type.*—Semi-double flowers present at nodes of lateral branches.

*Inflorescence size.*—Single flowers.

*Lastingness of flowers.*—About 5 days, self-cleaning.

*Flower size.*—An average of 5 cm in depth and 11.5 cm in diameter.

*Flower fragrance.*—None.

*Flower shape.*—Rotate.

*Flower number.*—An average of 28 per lateral stem (including secondary stems).

*Flower aspect.*—Slightly upright.

*Flower bud.*—Elliptic in shape, an average of 4 cm in length and 2.2 cm width just prior to opening, bract portion 137A in color, sepal portion 137B blending to 144A at margins, apex portion a blend of 71A, 70B, and 155A (towards base).

*Flower attachment.*—Peduncle.

*Petal and petaloid number.*—Average of 5 petals and 32 petaloid stamens.

*Petal and petaloid stamen shape.*—Petals; primarily orbicular, petaloid stamen; range from oblong to lanceolate.

*Petal and petaloid stamen color.*—Petals upper surface when newly opening; a blend of 63A, 63B, and 63C, eye zone; 185A with base 155A, veins N155B, petals lower surface when newly opening; a 63B, 63C, and 63D, blending at base to NN155D, very base 180A, veins N155A, petals fully open upper surface; N75A and slightly suffused towards apex with N79C, veins N155A, eye zone 180A (about 1.1 cm in length with feathered apex), 155A at very base, petals fully open lower surface; N75A and slightly suffused towards apex with N79C blending at base to 157C, veins N155A, very base 180A, petaloids when opening both surfaces; a blend of 63B and 63C, with veins 63D, and petaloids fully open both surfaces; 75A with veins N155.

*Petal and petaloid stamen surface.*—Both surfaces smooth and dull with center petaloids slight glossy on lower surface.

*Petal and petaloid stamen margins.*—Entire, slightly undulated.

*Petal attitude.*—Outer most petals slightly ascending, petaloids upright to curled in random directions.

*Petal and petaloid stamen apex.*—Petals; rounded, slightly undulate and slightly broadly crenate, petaloids; most have a single notch.

*Petal and petaloid stamen base.*—Petals; cuneate and truncate at very base, petaloids; acuminate.

*Petal and petaloid stamen size.*—Petals; average of 5.5 cm in length and width, petaloid stamens; average of 1.8 cm in length and 8 mm in width.

*Sepal number.*—5.

*Sepal shape.*—Fused base with triangular free portion.

*Sepal margin.*—Entire.

*Sepal size.*—Average of 2.2 cm in length and 1 cm in width, free portion is 1.1 cm in length and 1 cm in width at fusion point.

*Sepal aspect.*—Upright.

*Sepal surface.*—Outer surface finely puberulent, inner surface glabrous and glossy.

*Sepal apex.*—Narrowly acute.

*Sepal base.*—50% of base is fused.

*Sepal color.*—Young and mature outer surface; 137B blending to 144A at margins and at base, young and mature inner surface; a blend of 137D and 144A and 138C on margins.

*Calyx.*—Campanulate in shape, average of 2.2 cm in depth and 3.3 mm in diameter.

*Peduncles.*—An average of 3 cm in length and 3 mm in diameter, strong, held upward at about a 45° to the stem, 137D in color, surface glabrous but sparsely puberulent at apex.

*Pedicels.*—Not present, flowers are solitary from peduncles attached to stem.

*Bracts.*—5 bracts held close to calyx, linear in shape, narrowly acute to acuminate apex, truncate base, average of 1.9 cm in length and 2 mm in width, 137A in color on inner and outer surface, inner and outer surface is sparsely pubescent.

Reproductive organs:

*Gynoecium.*—1 pistil, stigma 5-lobed, round lobes about 2 mm in diameter, 155A in color, ovary; ovate in shape, 7 cm in length and 4 mm in diameter, NN155B in color.

*Androecium.*—Stamens; an average of 30 attached to the pollen tube, anthers; 1.5 mm in diameter, ovoid to irregular in shape, 161C in color, filaments; 3 mm in length and 1.5 mm in width, 155A in color, glandular surface, pollen tube; average of 3 cm in length and 2.5 mm in width at midpoint, pollen; very abundant and 9D in color.

*Fruit/seeds.*—None observed to date.

It is claimed:

1. A new and distinct cultivar of *Hibiscus* plant named 'Minsygdrou02' as herein illustrated and described.

* * * * *